(12) United States Patent
Ara et al.

(10) Patent No.: US 8,236,524 B2
(45) Date of Patent: Aug. 7, 2012

(54) MODIFIED MICROORGANISM

(75) Inventors: Katsutoshi Ara, Haga-gun (JP); Hiroshi Kakeshita, Haga-gun (JP); Kouji Nakamura, Tsukuba (JP)

(73) Assignee: Kao Corporation, Tokyo (JP)

( * ) Notice: Subject to any disclaimer, the term of this patent is extended or adjusted under 35 U.S.C. 154(b) by 165 days.

(21) Appl. No.: 12/530,710

(22) PCT Filed: Apr. 1, 2008

(86) PCT No.: PCT/JP2008/056842
§ 371 (c)(1),
(2), (4) Date: Sep. 10, 2009

(87) PCT Pub. No.: WO2008/123622
PCT Pub. Date: Oct. 16, 2008

(65) Prior Publication Data
US 2010/0093032 A1 Apr. 15, 2010

(30) Foreign Application Priority Data
Apr. 2, 2007 (JP) ................. 2007-096396

(51) Int. Cl.
*C12P 21/06* (2006.01)
*C12N 1/00* (2006.01)
(52) U.S. Cl. ................. 435/69.1; 435/243
(58) Field of Classification Search ............ None
See application file for complete search history.

(56) References Cited

FOREIGN PATENT DOCUMENTS

| JP | 2000-210081 A | 8/2000 |
|---|---|---|
| WO | WO 99/04006 | 1/1999 |
| WO | WO 99/04007 | 1/1999 |

OTHER PUBLICATIONS

Karamanou, S. et al., "*Escherichia coli* SecA truncated at its termini is functional and dimeric," FEBS Letters 579:1267-1271 (2005), Elsever B.V., The Netherlands (2005).*
Rajapandi et al. (Abstract-Carboxy-Terminal Region of *Escherichia coli* SecA ATPase Is Important to Promote Its Protein Translocation Activity in Vivo. vol. 200, issue 3, May 15, 1994, pp. 1477-1483 Was available online Apr. 29, 2002.*
The C-Terminus of SecA Is Involved in Both Lipid Binding and SecB Binding, Journal of Biological Chemistry vol. 270, Issue 14, pp. 7902-7907.*
Olmos-Soto, J., et al., "Genetic system constructed to overproduce and secrete proinsulin in *Bacillus subtilis*," Appl Microbiol Biotechnol 62:369-373, Springer Verlag, Germany (2003).

Vitikainen, M., et al., "Secretion of heterologous proteins in *Bacillus subtilis* can be improved by engineering cell components affecting post-translocational protein folding and degradation," *J. Appl Microbiol* 99:363-375, The Society for Applied Microbiology, United Kingdom (2005).
Hunt, J.F., et al., "Nucleotide Control of Interdomain Interactions in the Conformational Reaction Cycle of SecA," *Science* 297:2018-2026, American Association for the Advancement of Science, United States (2002).
Itaya, M., et al., "Gene-directed mutagenesis on the chromosome of *Bacillus subtilis* 168," *Mol Gen Genet* 223:268-272, Springer-Verlag, Germany (1990).
Karamanou, S. et al., "*Escherichia coli* SecA truncated at itts termini is functional and dimeric," *FEBS Letters* 579:1267-1271 (2005), Elsever B.V., The Netherlands (2005).
Kunst, F., et al., "The complete genome sequence of the gram-positive bacterium *Bacillus subtilis*," *Nature* 390:249-256, Nature Publishing Group, United Kingdom (1997).
Lipman, D.J., et al., "Rapid and sensitive protein similarity searches," *Science* 227:1435-1441, American Association for the Advancement of Science, United States (1985).
Na, B. et al., "Biochemical and mutational characterization of N-/C-terminal truncated *Escherichia coli* SecA mutants," *Abstracts of the General Meeting of the American Society for Microbiology*, vol. 105, p. 342, & 105th General Meeting of the American Society for Microbiology, Atlanta, GA, USA (Jun. 2005).
Shine, J., et al., "The 3'-Terminal Sequence of *Escherichia coli* 16S Ribosomal RNA: Complementarity to Nonsense Triplets and Ribosome Binding Sites," *Proc Natl Acad Sci USA* 71:1342-1346, United States (1974).
Vrontou, E., et al., "Global Co-ordination of Protein Translocation by the SecA IRA1 Switch," *J. Biol Chem* 279:22490-22497, The American Society for Biochemistry and Molecular Biology, Inc., United States (2004).
Yansura, D.G., et al., "Use of the *Escherichia coli lac* repressor and operator to control gene expression in *Bacillus subtilis*," *Proc Natl Acad Sci USA* 81:439-443, The National Academy of Sciences, United States (1984).
Van Wely, K.H.M., et al., "The carboxyl terminus of the *Bacillus subtilis* SecA is dispensable for protein secretion and viability," *Microbiology* 146: 2573-2581, Society for General Microbiology, Great Britain (2000).
International Search Report mailed Aug. 5, 2008, for PCT/JP2008/056842, European Patent Office, The Netherlands.
Esp@cenet Database, English language abstract of JP2000-210081 A (listed as document FP3 on the accompanying form PTO/SB/08A).

* cited by examiner

*Primary Examiner* — Kagnew H Gebreyesus
(74) *Attorney, Agent, or Firm* — Sterne, Kessler, Goldstein & Fox P.L.L.C.

(57) ABSTRACT

To provide a microorganism with enhanced secretory production of a protein or polypeptide and a method of producing the protein or polypeptide using the microorganism. A modified microorganism that has been genetically modified to delete 60 to 80 carboxyl-terminal amino acids of SecA.

10 Claims, 4 Drawing Sheets

MODIFIED MICROORGANISM

REFERENCE TO SEQUENCE LISTING SUBMITTED ELECTRONICALLY

The content of the electronically submitted substitute sequence listing, file name: SequenceListing.TXT; Size: 23,040 bytes; and Date of Creation: Sep. 4, 2009, filed herewith, is incorporated herein by reference in its entirety.

FIELD OF THE INVENTION

The present invention relates to a microorganism used for the production of a useful protein or polypeptide, and a method of producing such a protein or polypeptide.

BACKGROUND OF THE INVENTION

Microorganisms are used for industrial production of various useful substances, which include foods like alcoholic beverages, miso, and soy sauce, and also amino acids, organic acids, nucleic acid-related substances, antibiotics, saccharides, lipids, and proteins. These substances have wide ranging applications, such as in foods, drugs, detergents, cosmetics, and other items of daily use, and as raw materials for various chemical products.

Among microorganisms, gram-positive bacteria like *Bacillus subtilis*, *Bacillus licheniformis*, and *Bacillus megaterium* have a very high capacity to secrete a variety of exoenzymes such as amylases, proteases, and lipases. In fact, many exoenzymes produced by bacilli are presently in industrial use. Production of certain proteins by bacteria as secretions is useful in, for instance, that the secreted protein normally has its native structure, and the ease with which the secreted protein can be purified. Therefore, it is very meaningful to improve such bacterial strains in order to increase the amount of a given secretory protein secreted and produced.

Many of the proteins localized in the outer membrane and the periplasmic space of prokaryotes have passed through the cytoplasmic membrane mediated by a Sec translocation machinery. A transmembrane channel made of a heterotrimeric membrane protein complex consisting of SecY/SecE/SecG and a peripherally bound dimeric SecA, weakly bound to a SecD/SecF/YajD heterotrimeric membrane protein complex, is created, and the protein is translocated through the membrane with the help of energy from ATP hydrolysis by SecA. It is known that if the bacterium is *Escherichia coli*, the presecretory protein is recognized by the molecular chaperone SecB, and passed on to the SecA on the surface of the cytoplasmic membrane. The factor homologous with the molecular chaperone SecB has not yet been identified in *Bacillus subtilis* but it is believed that *Bacillus subtilis* has an SRP (signal recognition particle), characteristically involved in translocation across the endoplasmic reticulum membrane of eukaryotes, and that the secretory protein is handed over from the SRP to SecA. It has been shown that SecA of *Bacillus subtilis* consists of two domains, the N domain and the C domain, that the N domain has an ATP binding site I (ABS I) and a signal peptide binding site, that the C domain has sites that take part in SecA dimerization and interaction with SecY, and a region homologous with the SecB binding site of *Escherichia coli*, and that an ATP binding site II (ABS II) is present in a manner that aligns the two domains.

So far, genetic modifications such as deletion of a protease (Non-patent Document 1), enhancement of PrsA production (Non-patent Document 2), overexpression of SecD/SecE/SecDF (Patent Document 1), and overexpression of SecG (Patent Document 2) have been reported as techniques for increasing secretory production of proteins.

However, there has been no report on deletion of some of the amino acid residues of SecA for increasing secretory production of proteins.

[Non-patent Document 1] Olmos-Soto J, Contreras-Flores R. Genetic system constructed to overproduce and secrete proinsulin in *Bacillus subtilis*. Appl. Microbiol. Biotechnol. 2003 September; 62(4):369-73.

[Non-patent Document 2] Vitikainen M, Hyyrylainen H L, Kivimaki A, Kontinen V P, Sarvas M. Secretion of heterologous proteins in *Bacillus subtilis* can be improved by engineering cell components affecting post-translocational protein folding and degradation. J Appl Microbiol. 2005; 99(2): 363-75.

[Patent Document 1] WO99/04007
[Patent Document 2] WO99/04006

DISCLOSURE OF THE INVENTION

The present invention has the following aspects 1) to 3).

1) A microorganism genetically modified to delete 60 to 80 carboxyl-terminal amino acids of secA;

2) A recombinant microorganism constructed by introducing a gene encoding a heterologous protein or polypeptide into a strain of the modified microorganism; and 3) A method of producing a protein or polypeptide using the recombinant microorganism.

BEST MODE FOR CARRYING OUT THE INVENTION

The present invention relates to providing a microorganism with enhanced secretory production of a protein or polypeptide, and a method of producing the protein or polypeptide using the microorganism.

The present inventors examined the constituents of the secretory protein translocation machinery in bacilli, and found out that the capacity for secretory production improved when the gene was modified to delete 20 to 30 or 60 to 80, especially 60 to 80, carboxyl-terminal amino acids of SecA, and that such genetically modified microorganisms are useful in the production of proteins and polypeptides.

SecA is a factor involved in the secretion of secretory proteins to the outside of the bacterial cell. When SecA is deleted, not only is the production of protein reduced, but the cell itself dies also. Therefore, SecA is considered to be an essential factor of the secretion mechanism. Thus, the finding that the capacity for secretory production of protein by the bacterium improved when some of the amino acid residues of SecA were deleted was very unexpected.

The target protein or polypeptide can be produced efficiently by using the modified microorganism of the present invention, and the protein or polypeptide can be easily recovered from the culture fluid. Therefore, the present invention is useful for industrial production of the target protein or polypeptide.

In the present invention, the Lipman-Pearson method (Science, 227, 1435 (1985)) was used to determine the identity of the amino acid sequences and the base sequences. To be more specific, the search homology program of the genetic information processing software Genetyx-Win (Software Development) is used, and the analysis is carried out, taking the Unit Size to Compare (ktup) parameter as 2, to compute the homology.

The microorganism (host microorganism) of the present invention may be a gram-positive or a gram-negative bacterium, as long as it has a gene encoding SecA, but gram-positive bacteria are preferable, as they have the ability to produce proteins extracellularly by secretion. Among them, *Bacillus* is preferable, and *Bacillus subtilis* is particularly preferable, as its entire genomic information is available, and genetic engineering and genomic engineering techniques have been well established.

In the modified microorganism of the present invention, the target gene for modification is the gene encoding SecA.

SecA is one of the factors (proteins) involved in protein transport pathways in bacteria. It has the function of secreting the secretory protein outside the bacterial cells jointly with the transmembrane channel (SecY/SecE/SecG). *Bacillus subtilis* SecA (841 amino acids, molecular weight 95.3 KDa) consists of two domains, the N domain and the C domain. The N domain has the ATP-binding site I (ABS I), and a signal peptide binding site. The C domain has sites that take part in SecA dimerization and interaction with SecY, and a region homologous with the SecB binding site of *Escherichia coli*, and an ATP binding site II (ABS II) is known to be present in a manner that aligns the two domains.

*Bacillus subtilis* SecA and proteins functionally equivalent to it may be listed as examples of SecA suitable for modification in the present invention, and genes encoding *Bacillus subtilis* SecA or proteins functionally equivalent to it may be listed as examples of genes encoding SecA.

More specifically, "*Bacillus subtilis* SecA or proteins functionally equivalent to it" means a protein described in (A) to (C) below.

(A) A protein having an amino acid sequence represented by SEQ ID NO: 2;

(B) A protein having an amino acid sequence represented by SEQ ID NO: 2 with deletion, substitution, or addition of one or a few amino acids, and further having the same functions as SecA; and (C) A protein having an amino acid sequence with 80% or higher identity with the amino acid sequence represented by SEQ ID NO: 2, and further having the same functions as SecA.

Here, "amino acid sequence represented by SEQ ID NO: 2 with deletion, substitution, or addition of one or more amino acids" includes amino acid sequences with deletion, substitution, or addition of one or a few, preferably 1 to 10, amino acids, and "addition" here includes addition of 1 to a few amino acids at both the terminuses.

Here, "amino acid sequence with 80% or higher identity with the amino acid sequence represented by SEQ ID NO: 2" is preferably an amino acid sequence with 90% or more identity, more preferably 95% or more identity, and even more preferably 99% or more identity.

Furthermore, "having the same functions as SecA" means having functions that are practically the same as those of SecA, such as ATPase activity like SecA, and the capability to bind with the SecY/SecE complex.

Here, "genes encoding *Bacillus subtilis* SecA or proteins that are functionally equivalent to it" means genes that encode the proteins described in (A) to (C) above. But more preferably, it stands for genes described under (a) to (c) below.

(a) DNA having the base sequence represented by SEQ ID NO: 1;

(b) DNA that hybridizes under stringent conditions with DNA having a base sequence that is complimentary to the base sequence represented by SEQ ID NO: 1, and also encodes a protein having the same function as SecA; and (c) DNA having a base sequence with 80% or higher identity with the base sequence represented by SEQ ID NO: 1, and also encodes a protein having the same functions as SecA.

Here, the method described in Molecular Cloning—A LABORATORY MANUAL THIRD EDITION [Joseph Sambrook, David W. Russell, Cold Spring Harbor Laboratory-Press] may be cited as an example of "stringent conditions". For example, it can be the conditions of hybridization carried out, with a probe, in a solution containing 6×SSC (composition of 1×SSC: 0.15 M sodium chloride, 0.015 M sodium citrate, pH 7.0), 0.5% SDS, and 5×Denhardt's solution, and 100 mg/mL herring sperm DNA, for 8 to 16 h at the constant temperature of 65° C.

Here, "the base sequence with 80% or higher identity with the base sequence represented by SEQ ID NO: 1" is preferably a base sequence with 90% or more identity, more preferably 95% or more identity, and even more preferably 99% or more identity.

The DNA can be obtained from natural sources. But it is possible to prepare it using known techniques such as site-specific mutation induction. For example, it can be prepared by introducing mutations using the mutation induction kit [Mutant-super Express Km Kit (Takara)], which uses the method of site-specific mutation induction.

The gene sequence (SEQ ID NO: 1) encoding *Bacillus subtilis* SecA has been posted at JAFAN (Japan Functional Analysis Network for *Bacillus subtilis* (BSORF DB), bacillus.genome.ad.b, updated on Jan. 18, 2006), and genes that code for non-*Bacillus subtilis* SecA, such as of *Escherichia coli* are listed in the Colibri (genolist.pasteur.fr/Colibri/) database. A large number of genomes of gram-positive and gram-negative bacteria are posted at TIGER (cmr.tigr.org/tigr-scripts/CMR/cmrHomePage.cgi).

The number of carboxyl-terminal amino acids of SecA to be deleted in the present invention is 20 to 30 or 60 to 80. It is preferable to delete 60 to 80 amino acids.

In *Bacillus subtilis*, SecA consists of 841 amino acids (SEQ ID NO: 2). Deleting amino acids 820 to 841, inclusive, (also called N819) or deleting amino acids 781 to 841, inclusive, (also called N780), from SEQ ID NO: 2 is preferable. Deletion of amino acids 781 to 841, inclusive, (N780) is more preferable.

*Bacillus subtilis* SecA has, at its carboxyl terminus, a CTD region (C-Terminal region Domain; see J. B. C. (2004) 279 (21), p 22490-22497). Twenty-two C-terminal amino acids of the CTD region constitute the region homologous with the SecB binding site of *Escherichia coli*, and the CTD region has, at its N-terminus, a region consisting of 61 amino acids called the CTL region (C-Terminal Terminal Linker; see Science (2002) 297 (5589), p 2018-2026). In *Bacillus subtilis*, binding with Ffh (Fifty Four Homologue, SRP 54 homologue), which is a constituent of the signal recognition particle (SRP), occurs in this region. Incidentally, the regions of CTL, which corresponds to the region of Ffh binding falls in the region of amino acids 781 to 819.

Therefore, the genetic modification of the present invention includes the deletion of the aforesaid regions, or regions homologous with them, singly or in combinations, and it is preferable that the genetic modification delete the Ffh binding region or a region homologous with it.

The method of homologous recombination may be used, for instance, as the method of modifying the gene encoding SecA, in the present invention. In other words, the DNA fragment containing a part of the target gene may be cloned in a suitable plasmid vector and the circular recombinant plasmid thus obtained may then be incorporated into the cell of a parent microorganism. Then, by homologous recombination at a region that is a part of the target gene, the target segment of the secA gene in the genome of the parent microorganism may be cut for the deletion.

Especially when using *Bacillus subtilis* as the parent microorganism for constructing the microorganism of the present invention, because there are several reported methods of deleting target genes by homologous recombination (Mol. Gen. Genet., 223, 268, 1990, etc) any such method may be used for producing the host microorganism of the invention.

In the following part, we shall describe more specifically the method of deleting a part of SecA, using a DNA fragment prepared by recombinant DNA technology.

The DNA fragment used for deleting a part of SecA is a gene sequence in which the gene region at the 3' end of secA gene is partially modified. It has at least one restriction enzyme recognition site at each end. The DNA fragment can be prepared by a standard method using these restriction enzyme sites, for instance, through PCR-amplification using *Bacillus subtilis* genomic DNA as the template, and primers containing these restriction enzyme sites. Moreover, the 3' end primer of the DNA fragment has an inserted genetic sequence encoding a stop codon immediately upstream of the gene encoding the C-terminal region of the SecA protein that is targeted for deletion.

To construct a plasmid, this fragment is inserted at the multi-cloning site of an integration vector such as pDH88, etc that enables homologous recombination through genetic transformation of a genetically transformable gram-positive bacterium like *Bacillus subtilis*.

Figure 1:
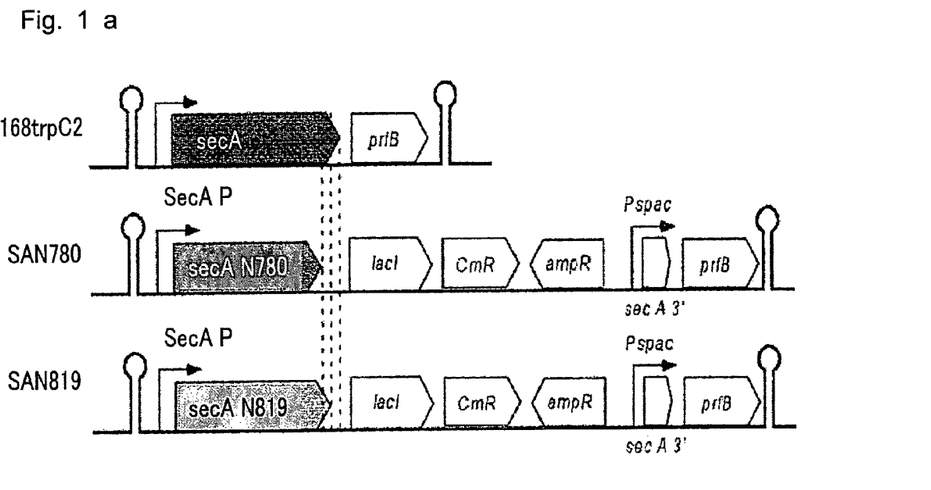
FIG. 1a is an illustration of the genomic structure around the secA gene locus of strains SAN819 and SAN780.
FIG. 1b is an electrophoresis pattern that confirms the sizes of SecA expressed in strains SAN819 and SAN780.

By introducing the plasmid into *Bacillus subtilis*, or the like, and carrying out homologous recombination, we can obtain a strain (strain with partially deleted SecA) where the plasmid is incorporated into the chromosome. The genomic structure on the chromosome of the strain thus obtained is illustrated in FIG. 1a. In the strains having the insertion, the translation of the SecA protein expressed on the chromosome is halted midway because of the stop codon located before of the region to be deleted. Therefore, only the desired protein lacking the C-terminal region of SecA can be expressed.

The recombinant microorganism of the present invention can be obtained by introducing, into a strain of the modified microorganism thus obtained, a gene that codes for the desired heterologous protein or polypeptide.

There is no particular restriction on the target protein or polypeptide to be produced by the recombinant microorganism of the present invention. For instance, it can be a physiologically active peptide, or an industrial enzyme used in detergents, foods, fibers, feeds, chemical products, medical and diagnostic products, etc.

Examples of physiologically active peptides include proteins encoded by the genomes of pathogenic viruses, such as hepatitis B virus, hepatitis C virus, HIV, and influenza virus, and G-protein conjugate receptor, growth factors (platelet growth factor, blood stem cell growth factor, liver cell growth factor, transforming growth factor, nerve growth/trophic factor, fibroblast growth factor, insulin-like growth factor, etc), tumor necrosis factor, interferon, interleukin, erythropoietin, granulocyte colony-stimulating factor, macrophage colony-stimulating factor, albumin, and human growth hormone.

Industrially used enzymes include oxidoreductases, transferases, hydrolases, lyases, isomerases, and ligases/synthetases, and more suitably, hydrolases like cellulase, α-amylase, and protease.

The gene of the target protein or polypeptide introduced into the microorganism of the present invention preferably has, on its upstream side, control regions concerned with the gene's transcription, and subsequent translation and secretion. In other words, it preferably has one or more suitably combined regions selected from a transcription initiation control region, which includes a promoter and transcription initiation point, a translation initiation region that includes a ribosome binding site and a start codon, and a secretion signal peptide region.

Here, the transcription initiation control region is a region that includes a promoter, and a transcription initiation point, and the ribosome binding site is the site corresponding to the Shine-Dalgarno (SD) sequence (Proc. Natl. Acad. Sci. USA 74, 5463 (1974)), which along with the start codon forms the translation initiation control region.

The aforesaid DNA fragment containing the gene of the desired heterologous protein or polypeptide, and a suitable plasmid vector are combined to form a recombinant plasmid. The recombinant microorganism of this invention can be obtained by introducing this recombinant plasmid into the host microbial cell by ordinary techniques of genetic transformation. The recombinant microorganism of the present invention can also be obtained by directly incorporating the aforesaid DNA fragment, to which a suitable region homologous with the genome of the host microorganism is bound, into the genome of the host microorganism.

Production of the desired protein or polypeptide using the recombinant microorganism of the present invention may be undertaken by inoculating the bacterial strain in a medium containing assimilable carbon and nitrogen sources and other essential components, culturing by an ordinary method of microbial culturing, and harvesting and purifying the protein or polypeptide after the culturing. As is demonstrated in the examples described later, the productivity of the target protein or polypeptide is increased, compared to cases where microorganisms with genetically unmodified SecA are used.

Next, we shall describe in more detail the method of constructing the recombinant microorganism of the present invention, and the method of producing a protein using the recombinant microorganism.

EXAMPLES

Bacterial Strains, Plasmids, and Media Used (1) Bacterial Strains Used
*Bacillus subtilis* strain Marburg 168trpC2 (Kunst et al. Nature 1997)
*Bacillus subtilis* strain SAN819 (N819); resistance marker (chloramphenicol)
*Bacillus subtilis* strain SAN780 (N780); resistance marker (chloramphenicol)
*Escherichia coli* strain C600 (Takara Bio)
*Escherichia coli* strain JM109 (Takara Bio)
(2) Plasmids
pDH88; Henner et. al. (Proc Natl Acad Sci USA. 1984 January 81(2): 439-43), resistance markers (ampicillin and chloramphenicol).
pHKK1101; resistance markers (ampicillin and chloramphenicol), recombinant vector for creating a strain with partially deleted SecA (strain SAN819)
pHKK1002; Resistance markers (ampicillin and chloramphenicol), recombinant vector for creating a strain with partially deleted SecA (strain SAN780)
pWH1520; MoBiTec, resistant markers (ampicillin and tetracycline)
pHKK3200; resistance markers (ampicillin and tetracycline), inserted genes (amylase AmyE signal peptide and pro region)
pHKK3201; resistance markers (ampicillin and tetracycline), inserted genes (fused protein of amylase AmyE signal peptide and pro region, and IFN a mature region)
pHKK3202; resistance markers (ampicillin and tetracycline), inserted genes (fused protein of the amylase AmyE signal peptide, and pro region, and IFN mature region)
(3) Media
L medium: Bactotryptone (Difco) 1%, yeast extract (Difco) 0.5%, NaCl (Wako) 0.5%
2×L medium: Bactotryptone (Difco) 2%, yeast extract (Difco) 1%, NaCl (Wako) 1%

The concentrations of antibiotics used were 15 μg of chloramphenicol and 50 μg of ampicillin. A final xylose concentration of 0.6% was used for the induction of xylose promoter present in pWH1520. Isopropyl-β-thiogalactopyranoside (IPTG) was used at a final concentration of 100 μM.

Example 1

Construction of Plasmids and Strains with Partially Deleted SecA (1) Recombinant Vectors for Creating Strains with Partially Deleted SecA To create the *Bacillus subtilis* strain SAN819, firstly, a 360 bp segment at the 3' end of the secA gene was amplified by PCR using the chromosome of *Bacillus subtilis* strain 168 as the template, and secAC-01

(gatcAAGCTTcccgggagaagagcgatatcttcgg, (SEQ ID NO: 3)

the upper case letters represent HindIII) and secAC-02

(gatcagaTCTAGAttaaatctcagctttcatcacaaa, (SEQ ID NO: 4)

the upper case letters represent XbaI, the underlined letters represent the inserted stop codon) as primers. The amplified segment was then inserted at the HindIII-XbaI site of pDH88 to construct pHKK1001. Similarly, to create the *Bacillus subtilis* strain SAN780, pHKK1002 was constructed using the primers secAC-03

(gatcAAGCTTcccgggagaagagcgatatcttcgg, (SEQ ID NO: 5)

the upper case letters represent HindIII) and secAC-04

(gatcagaTCTAGAttagatatcaaccactttgcgaac, (SEQ ID NO: 6)

the upper case letters represent XbaI, underlined letters represent the inserted stop codon).

(2) Creation of Strains with Partially Deleted SecA

*Bacillus subtilis* strain SAN819 was obtained by Campbell incorporation of the plasmid pHKK1001 into the chromosome of *Bacillus subtilis* strain 168 (FIG. 1a). Strain SAN780 was also obtained by a similar method, using the plasmid pHKK1002. That these plasmids were properly incorporated into the chromosomes of SAN819 and SAN780 respectively was confirmed by Southern hybridization analysis. The size of SecA expressed in strains SAN819 and SAN780 was also confirmed using anti-SecA antibodies (FIG. 1b).

(3) Effect on Growth of Strains with Partially Deleted SecA

The effect on growth was observed in the strains SAN819 and SAN780 created in (2). L liquid medium, L plate medium, and 2×L liquid medium were used for the culture (IPTG was added to the final concentration of 100 μM in all cases). Culturing was done at 30° C., 37° C., and 47° C.

The results showed that the *Bacillus subtilis* strains SAN819 and SAN780 had growth comparable to the parent strain, *Bacillus subtilis* strain 168, under all the conditions tested.

Growth was suppressed when no IPTG was added, because of the effect of the prfB gene located downstream of secA, which forms an operon with secA.

These facts reveal that the CTD (C-Terminal region domain) region, which is the C-terminal region of SecA, is not essential to the growth of *Bacillus subtilis*.

Example 2

Expression of Heterologous Protein (1) Construction of a Vector for Expressing Heterologous Protein A signal sequence is required for secretion of the heterologous protein outside the cell. Therefore, the basic vector pHKK3200 for expression of the secretory protein, having the signal sequence and the pro sequence of the *Bacillus subtilis* amylase (amyE) protein was created. To create pHKK3200, the 175 bp coding region of the amyE gene signal sequence, and the pro sequence was PCR-amplified using the chromosome of *Bacillus subtilis* strain 168 as the template, and amyESF-1

(ggccACTAGTcttcaaaaaatcaaa, (SEQ ID NO: 7)

the upper case letters represent SpeI) and amyESR-2

(ggccGGTACCctcattcgatttgttcgc, (SEQ ID NO: 8)

the upper case letters represent KpnI) as primers, and the amplified product was inserted into the SpeI-KpnI site of pWH1520.

To create the interferon-α expressing plasmid, the 521 bp segment containing the ifnα gene mature region was PCR-amplified using pORF5-hIFN-α (InvivoGen) as the template, and ifnaF

```
(ggccGGTACCctcctggtgctcagctgc, (SEQ ID NO: 9)
``` the upper case letters represent KpnI) and ifnaR

Figure 2:
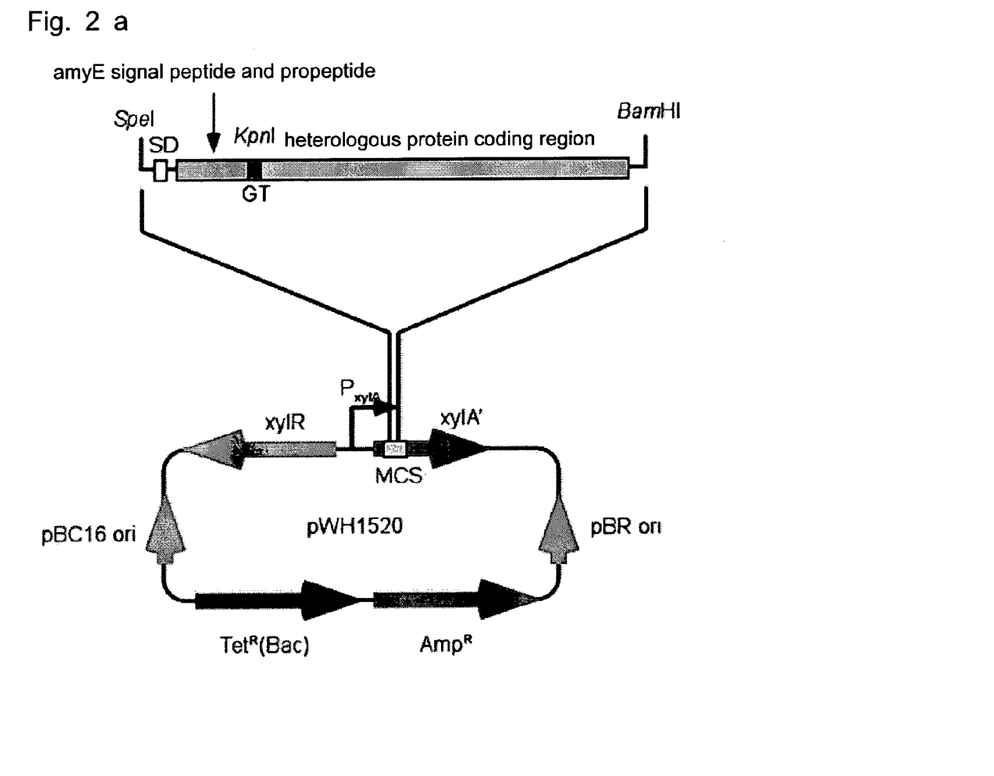
FIG. 2a is an illustration of the method of constructing an interferon expression vector.
FIG. 2b is an illustration of the structure of the fused protein of *Bacillus subtilis* amylase AmyE signal peptide, and the pro sequence, and of the interferon-α mature region, introduced into the interferon expression vector pHKK3201.

```
(ggccGGATCCttttcattccttacttct, (SEQ ID NO: 10)
``` the upper case letters represent BamHI) as the primers, and inserted into the KpnI-BamHI site of pHKK3200 thereby constructing pHKK3201 (FIGS. 2a) and b)).

By a similar procedure, the interferon-β expressing plasmid pHKK3202 was created using pORF-hIFN-β (InvivoGen) as the template, and ifnbF

```
(ggccGGTACCatgagctacaactt, (SEQ ID NO: 11)
``` the upper case letters represent KpnI) and ifnbR

```
(ggccGGATCCagctcagtttcggaggta, (SEQ ID NO: 12)
``` the upper case letters represent BamHI) as primers.

(2) Creation of Strains into which a Heterologous Protein Expression Vector has been Incorporated The interferon-α express vector pHKK3201 and the interferon-β expressing plasmid pHKK3202 created in (1) were respectively incorporated by the method of genetic transformation into the strains SAN780 and SAN819 to obtain interferon expression vector-incorporated strains.

The genetic transformation was carried out by a competent method using the SPI and SPII media, and the bacterial strains that grew in the LB agar medium containing 15 μg/mL of chloramphenicol were taken as the transformed strains.

(3) Culturing

The 2×L medium (2% Tripton (Difco), 1% yeast extract (Difco), 1% NaCl) was used. Tetracycline (Wako) was added to a final concentration of 15 μg/mL when required. The medium was inoculated with 2% of the preparatory culture, and cultured at 30° C. until the mid-phase of cell multiplication (OD660=0.3), xylose was added to a final concentration of 0.6%, and the culturing was continued. The bacterial cells were separated and the culture fluid obtained 24 h after the start of culturing.

The interferon-containing sample was analyzed by Western blotting, and the intensity of the detected bands was measured and used for comparison.

(4) Confirmation of the Secretory Protein (Interferon (IFN))
1) Western Blotting Western blotting was carried out using a semi-dry system (Bio-Rad). After separating the proteins by SDS-PAGE, they were transferred to an Immobilon PVDF membrane (Millipore). The proteins were detected using an ECL detection system (Amersham, now GE Healthcare).

The anti-interferon-α and anti-interferon-β antibodies used were products of PeproTech EC LTD. The HRP-labeled secondary antibodies used were products of Amersham (now GE Healthcare).

2) Measurement of Interferon Activity

The culture fluid from which cells had been removed by centrifuging after 24 h of culturing was used as the interferon-containing sample. Xylose was added to a final concentration of 0.6% at the time when OD660 became 0.3 after the start of culturing, for inducing the interferon. Physiological activity of interferon in the culture fluid was measured using animal cells. This experimental measurement was contracted to Mitsubishi BCL. The interferon secreted by the action of the interferon expression vector used in this experiment had physiological activity.

(5) Method of Evaluating the Amounts Secreted

The culture fluid was developed by SDS-PAGE, the proteins were blotted on to a PVDF membrane, and detected by the Western blotting method using IFNα antibody (Pepro-Tech EC LTD). The intensity of the band obtained by Western blotting was converted into a numerical value using NIH Image (National Institutes of Health, USA), for measuring of the amount secreted. The amount produced when the mutant strain was the host was evaluated as a relative value with reference to the control, i.e., the amount produced when the wild type strain was the host.

(6) Results

Figure 3:
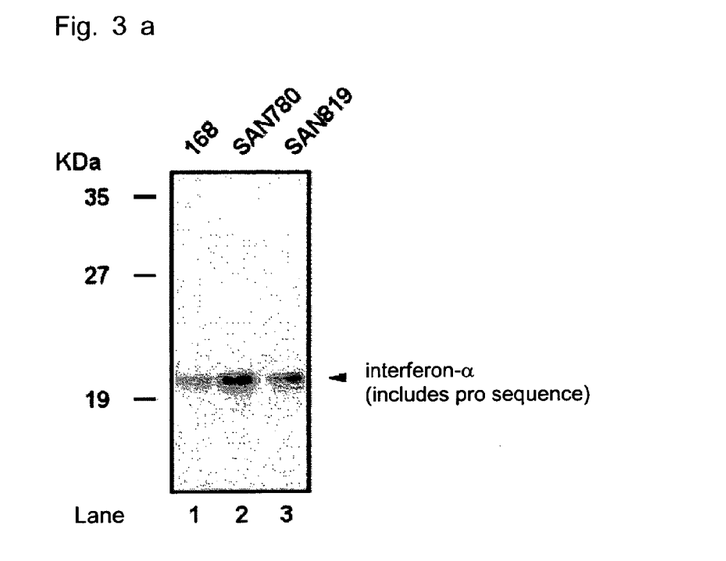
FIG. 3a is an illustration of the result of detection, by Western blotting, of interferon-α produced after introduction of pHKK3201 into the host strains SAN780 and SAN819; Lane 1: When the parent strain 168 was the host. Lane 2: When strain ASN780 was the host. Lane 3: When strain ASN819 was the host.
FIG. 3b is a graphic representation of the results of the experiment of FIG. 3a; The relative IFN alpha protein amounts were compared on the basis of band intensities on Western blots. The amount of IFN α in the wild type strain was set to 100%, The Error bars represent standard deviations.
Figure 4:
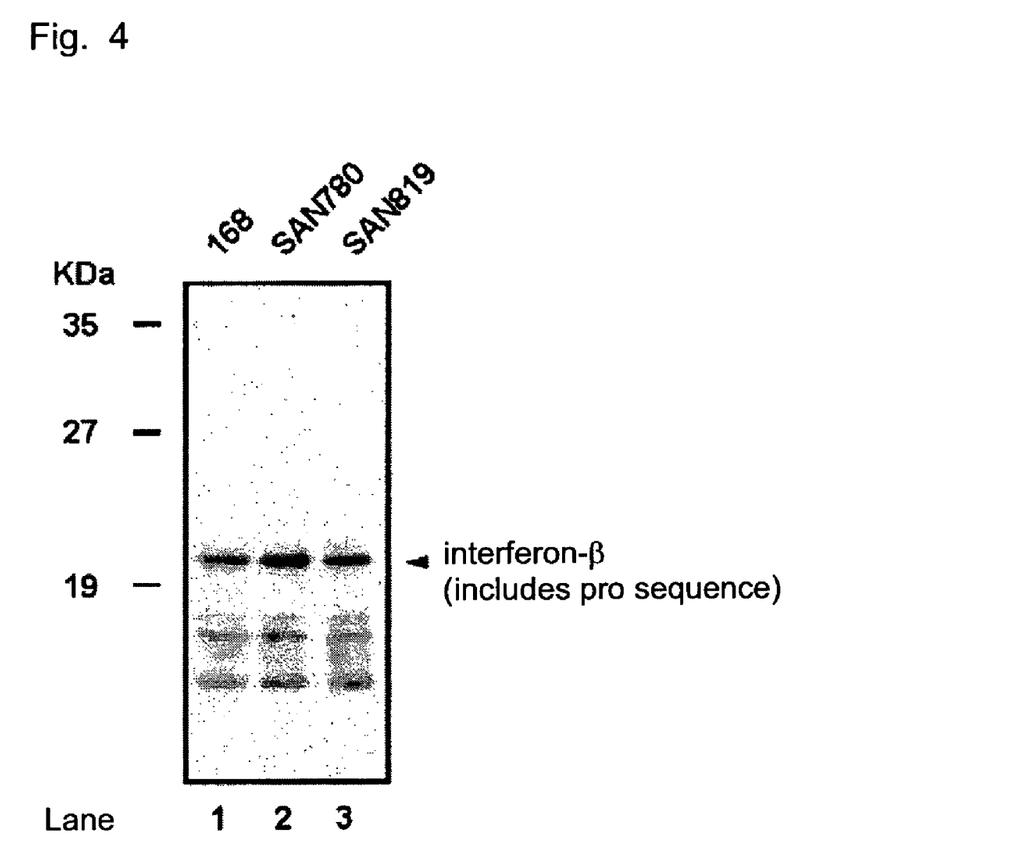
FIG. 4 is an illustration of the result of detection, by Western blotting, of interferon-β produced after introduction of the pHKK3202 into the host strains SAN780 and SAN819; Lane 1: When the parent strain 168 was the host. Lane 2: When strain ASN780 was the host. Lane 3: When strain ASN819 was the host.

The amounts of interferon-α produced by the strains SAN780 and SAN819 were greater than that produced by the parent strain 168 (FIG. 3). A similar improvement was seen in the production of interferon-β (FIG. 4).

(7) Evaluation of Cellulase Production

A recombinant plasmid pHY-S237 was introduced, by the method of genetic transformation of protoplasts, into strain SAN780, and also *Bacillus subtilis* strain 168 as control. The recombinant plasmid had been produced by inserting a DNA fragment (3.1 kb) encoding the alkaline cellulase gene derived from the *Bacillus* strain KSM-S237 (FERMBP-7875) (see Japanese Patent Laid-Open No. 2000-210081) into the restriction enzyme site BamHI of the shuttle vector pHY300PLK.

The genetically transformed strain thus obtained was subjected to shake culturing for 15 h at 30° C. in 5 mL of the LB medium. 0.6 mL of this culture fluid was inoculated into 30 mL of 2×L maltose medium (2% tryptone, 1% yeast extract, 1% sodium chloride, 7.5% maltose, 7.5 ppm manganese sulfate 4-5 hydrate, and 15 ppm tetracycline), and shake cultured for 3 days at 30° C. After culturing, the bacterial cells were removed by centrifuging, and the alkaline cellulase activity of the supernatant of the culture fluid was measured either by the method given in the aforesaid patent reference or by measuring the change in absorbance (420 nm) at pH 7.0 and temperature 30° C., using p-nitrophenyl-β-cellotrioside (Seikagaku Corp.) as the substrate, and the amount of secreted alkaline cellulase produced outside the bacterial cells was determined. The results are given in Table 1.

TABLE 1

| Bacterial strain | SecA | Amount of alkaline cellulase secreted and produced (relative value) |
|---|---|---|
| Strain 168 | Wild type (1-841) | 100 |
| Strain SAN780 | 1-780 | 125 |

As shown in Table 1, there was higher secretory production of alkaline cellulase when the strain SAN780 was the host, compared to the control where strain 168 (wild type) was the host.

The invention claimed is:

1. A method of producing a heterologous protein or polypeptide comprising:

i. culturing a modified *Bacillus* microorganism comprising a modified gene encoding a modified SecA protein that replaces the endogenous SecA gene and a gene encoding the heterologous protein or polypeptide in a culture medium under conditions that permit expression of the gene encoding the heterologous protein or polypeptide; and ii. collecting the heterologous protein or polypeptide from the culture medium; wherein said modified SecA protein is derived from a non-modified SecA protein in which 60-80 carboxyl-terminal amino acids of said non, modified SecA protein have been deleted, said non-modified SecA is selected from the group consisting of:

(A) A protein having the amino acid sequence of SEQ ID NO: 2;

(B) A protein having the amino acid sequence of SEQ ID NO: 2 with deletion, substitution or addition of 1 to 10 amino acids, and further having the same functions as SecA; and (C) A protein having an amino acid sequence with 95% or higher identity with the amino acid sequence of SEQ ID NO: 2 and further having the same functions as SecA.

2. The method according to claim 1 wherein the *Bacillus* is a *Bacillus subtilis*.

3. The method according to claim 1, wherein the amino acid sequence of said modified SecA protein is the amino acid sequence of SEQ ID NO:2 except that amino acids 781 to 841, inclusive, have been deleted.

4. The method according to claim 1, wherein said deletion of said carboxyl-terminal amino acids of said non-modified SecA protein is the deletion of the Ffh binding region or a region homologous with it.

5. The method according to claim 1, wherein the amino acid sequence of said non-modified SecA protein in said modified *Bacillus* microorganism consists of the amino acid sequence of SEQ ID NO:2.

6. The method according to claim 1, wherein the amino acid sequence of said non-modified SecA protein in said modified *Bacillus* microorganism consists of the amino acid sequence of SEQ ID NO: 2 with deletion, substitution or addition of 1 to 10 amino acids, and further having the same functions as SecA.

7. The method according to claim 1, wherein the amino acid sequence of said non-modified SecA protein in said modified *Bacillus* microorganism consists of an amino acid sequence with 95% or higher identity with the amino acid sequence of SEQ ID NO: 2, and further having the same functions as SecA.

8. The method of claim 1 wherein the productivity of the heterologous protein or polypeptide is increased compared to *Bacillus* microorganisms in which the endogenous SecA is not replaced by a modified SecA.

9. The method of claim 3 wherein the productivity of the heterologous protein or polypeptide is increased compared to *Bacillus* microorganisms in which the endogenous SecA is not replaced by a modified SecA.

10. The method of claim 4 wherein the productivity of the target heterologous protein or polypeptide is increased compared to *Bacillus* microorganisms in which the endogenous SecA is not replaced by a modified SecA.

* * * * *

UNITED STATES PATENT AND TRADEMARK OFFICE
CERTIFICATE OF CORRECTION

PATENT NO. : 8,236,524 B2
APPLICATION NO. : 12/530710
DATED : August 7, 2012
INVENTOR(S) : Katsutoshi Ara, Hiroshi Kakeshita and Kouji Nakamura

Page 1 of 1

It is certified that error appears in the above-identified patent and that said Letters Patent is hereby corrected as shown below:

In the Claims:

In col. 23, claim 1, lines 63-64, change "said non, modified Sec A" to read "said non-modified SecA."

Signed and Sealed this
Eighth Day of January, 2013

David J. Kappos
*Director of the United States Patent and Trademark Office*

SEQUENCE LISTING

<160> NUMBER OF SEQ ID NOS: 12

<210> SEQ ID NO 1
<211> LENGTH: 2523
<212> TYPE: DNA
<213> ORGANISM: Bacillus subtilis
<220> FEATURE:
<221> NAME/KEY: CDS
<222> LOCATION: (1)..(2523)
<223> OTHER INFORMATION:

<400> SEQUENCE: 1

```
atg ctt gga att tta aat aaa atg ttt gat cca aca aaa cgt acg ctg      48
Met Leu Gly Ile Leu Asn Lys Met Phe Asp Pro Thr Lys Arg Thr Leu
1               5                   10                  15 aat aga tac gaa aaa att gct aac gat att gat gcg att cgc gga gac      96
Asn Arg Tyr Glu Lys Ile Ala Asn Asp Ile Asp Ala Ile Arg Gly Asp
            20                  25                  30 tat gaa aat ctc tct gac gac gca ttg aaa cat aaa aca att gaa ttt     144
Tyr Glu Asn Leu Ser Asp Asp Ala Leu Lys His Lys Thr Ile Glu Phe
        35                  40                  45 aaa gag cgt ctt gaa aaa ggg gcg aca acg gat gat ctt ctt gtt gaa     192
Lys Glu Arg Leu Glu Lys Gly Ala Thr Thr Asp Asp Leu Leu Val Glu
    50                  55                  60 gct ttc gct gtt gtt cga gaa gct tca cgc cgc gta aca ggc atg ttt     240
Ala Phe Ala Val Val Arg Glu Ala Ser Arg Arg Val Thr Gly Met Phe
65                  70                  75                  80 ccg ttt aaa gtc cag ctc atg ggg ggc gtg gcg ctt cat gac gga aat     288
Pro Phe Lys Val Gln Leu Met Gly Gly Val Ala Leu His Asp Gly Asn
                85                  90                  95 ata gcg gaa atg aaa aca ggg gaa ggg aaa aca tta acg tct acc ctg     336
Ile Ala Glu Met Lys Thr Gly Glu Gly Lys Thr Leu Thr Ser Thr Leu
            100                 105                 110 cct gtt tat tta aat gcg tta acc ggt aaa ggc gta cac gtc gtg act     384
Pro Val Tyr Leu Asn Ala Leu Thr Gly Lys Gly Val His Val Val Thr
        115                 120                 125 gtc aac gaa tac ttg gca agc cgt gac gct gag caa atg ggg aaa att     432
Val Asn Glu Tyr Leu Ala Ser Arg Asp Ala Glu Gln Met Gly Lys Ile
    130                 135                 140 ttc gag ttt ctc ggt ttg act gtc ggt ttg aat tta aac tca atg tca     480
Phe Glu Phe Leu Gly Leu Thr Val Gly Leu Asn Leu Asn Ser Met Ser
145                 150                 155                 160 aaa gac gaa aaa cgg gaa gct tat gcc gct gat att act tac tcc aca     528
Lys Asp Glu Lys Arg Glu Ala Tyr Ala Ala Asp Ile Thr Tyr Ser Thr
                165                 170                 175 aac aac gag ctt ggc ttc gac tat ttg cgt gac aat atg gtt ctt tat     576
Asn Asn Glu Leu Gly Phe Asp Tyr Leu Arg Asp Asn Met Val Leu Tyr
            180                 185                 190 aaa gag cag atg gtt cag cgc ccg ctt cat ttt gcg gta ata gat gaa     624
Lys Glu Gln Met Val Gln Arg Pro Leu His Phe Ala Val Ile Asp Glu
        195                 200                 205 gtt gac tct att tta att gat gaa gca aga aca ccg ctt atc att tct     672
Val Asp Ser Ile Leu Ile Asp Glu Ala Arg Thr Pro Leu Ile Ile Ser
    210                 215                 220 gga caa gct gca aaa tcc act aag ctg tac gta cag gca aat gct ttt     720
Gly Gln Ala Ala Lys Ser Thr Lys Leu Tyr Val Gln Ala Asn Ala Phe
225                 230                 235                 240 gtc cgc acg tta aaa gcg gag aag gat tac acg tac gat atc aaa aca     768
Val Arg Thr Leu Lys Ala Glu Lys Asp Tyr Thr Tyr Asp Ile Lys Thr
                245                 250                 255
```

-continued

| | | |
|---|---|---|
| aaa gct gta cag ctt act gaa gaa gga atg acg aag gcg gaa aaa gca<br>Lys Ala Val Gln Leu Thr Glu Glu Gly Met Thr Lys Ala Glu Lys Ala<br>260           265           270 | 816 | |
| ttc ggc atc gat aac ctc ttt gat gtg aag cat gtc gcg ctc aac cac<br>Phe Gly Ile Asp Asn Leu Phe Asp Val Lys His Val Ala Leu Asn His<br>275           280           285 | 864 | |
| cat atc aac cag gcc tta aaa gct cac gtt gcg atg caa aag gac gtt<br>His Ile Asn Gln Ala Leu Lys Ala His Val Ala Met Gln Lys Asp Val<br>290           295           300 | 912 | |
| gac tat gta gtg gaa gac gga cag gtt gtt att gtt gat tcc ttc acg<br>Asp Tyr Val Val Glu Asp Gly Gln Val Val Ile Val Asp Ser Phe Thr<br>305           310           315           320 | 960 | |
| gga cgt ctg atg aaa ggc cgc cgc tac agt gag ggg ctt cac caa gcg<br>Gly Arg Leu Met Lys Gly Arg Arg Tyr Ser Glu Gly Leu His Gln Ala<br>325           330           335 | 1008 | |
| att gaa gca aag gaa ggg ctt gag att caa aac gaa agc atg acc ttg<br>Ile Glu Ala Lys Glu Gly Leu Glu Ile Gln Asn Glu Ser Met Thr Leu<br>340           345           350 | 1056 | |
| gcg acg att acg ttc caa aac tac ttc cga atg tac gaa aaa ctt gcc<br>Ala Thr Ile Thr Phe Gln Asn Tyr Phe Arg Met Tyr Glu Lys Leu Ala<br>355           360           365 | 1104 | |
| ggt atg acg ggt aca gct aag aca gag gaa gaa gaa ttc cgc aac atc<br>Gly Met Thr Gly Thr Ala Lys Thr Glu Glu Glu Glu Phe Arg Asn Ile<br>370           375           380 | 1152 | |
| tac aac atg cag gtt gtc acg atc cct acc aac agg cct gtt gtc cgt<br>Tyr Asn Met Gln Val Val Thr Ile Pro Thr Asn Arg Pro Val Val Arg<br>385           390           395           400 | 1200 | |
| gat gac cgc ccg gat tta att tac cgc acg atg gaa gga aag ttt aag<br>Asp Asp Arg Pro Asp Leu Ile Tyr Arg Thr Met Glu Gly Lys Phe Lys<br>405           410           415 | 1248 | |
| gca gtt gcg gag gat gtc gca cag cgt tac atg acg gga cag cct gtt<br>Ala Val Ala Glu Asp Val Ala Gln Arg Tyr Met Thr Gly Gln Pro Val<br>420           425           430 | 1296 | |
| cta gtc ggt acg gtt gcc gtt gaa aca tct gaa ttg att tct aag ctg<br>Leu Val Gly Thr Val Ala Val Glu Thr Ser Glu Leu Ile Ser Lys Leu<br>435           440           445 | 1344 | |
| ctt aaa aac aaa gga att ccg cat caa gtg tta aat gcc aaa aac cat<br>Leu Lys Asn Lys Gly Ile Pro His Gln Val Leu Asn Ala Lys Asn His<br>450           455           460 | 1392 | |
| gaa cgt gaa gcg cag atc att gaa gag gcc ggc caa aaa ggc gca gtt<br>Glu Arg Glu Ala Gln Ile Ile Glu Glu Ala Gly Gln Lys Gly Ala Val<br>465           470           475           480 | 1440 | |
| acg att gcg act aac atg gcg ggg cgc gga acg gac att aag ctt ggc<br>Thr Ile Ala Thr Asn Met Ala Gly Arg Gly Thr Asp Ile Lys Leu Gly<br>485           490           495 | 1488 | |
| gaa ggt gta aaa gag ctt ggc ggg ctc gct gta gtc gga aca gaa cga<br>Glu Gly Val Lys Glu Leu Gly Gly Leu Ala Val Val Gly Thr Glu Arg<br>500           505           510 | 1536 | |
| cat gaa tca cgc cgg att gac aat cag ctt cga ggt cgt tcc gga cgt<br>His Glu Ser Arg Arg Ile Asp Asn Gln Leu Arg Gly Arg Ser Gly Arg<br>515           520           525 | 1584 | |
| cag gga gac ccg ggg att act caa ttt tat ctt tct atg gaa gat gaa<br>Gln Gly Asp Pro Gly Ile Thr Gln Phe Tyr Leu Ser Met Glu Asp Glu<br>530           535           540 | 1632 | |
| ttg atg cgc aga ttc gga gct gag cgg aca atg gcg atg ctt gac cgc<br>Leu Met Arg Arg Phe Gly Ala Glu Arg Thr Met Ala Met Leu Asp Arg<br>545           550           555           560 | 1680 | |
| ttc ggc atg gac gac tct act cca atc caa agc aaa atg gta tct cgc<br>Phe Gly Met Asp Asp Ser Thr Pro Ile Gln Ser Lys Met Val Ser Arg<br>565           570           575 | 1728 | |

```
gcg gtt gaa tcg tct caa aaa cgc gtc gaa ggc aat aac ttc gat tcg    1776
Ala Val Glu Ser Ser Gln Lys Arg Val Glu Gly Asn Asn Phe Asp Ser
        580                 585                 590 cgt aaa cag ctt ctg caa tat gat gat gtt ctc cgc cag cag cgt gag    1824
Arg Lys Gln Leu Leu Gln Tyr Asp Asp Val Leu Arg Gln Gln Arg Glu
            595                 600                 605 gtc att tat aag cag cgc ttt gaa gtc att gac tct gaa aac ctg cgt    1872
Val Ile Tyr Lys Gln Arg Phe Glu Val Ile Asp Ser Glu Asn Leu Arg
        610                 615                 620 gaa atc gtt gaa aat atg atc aag tct tct ctc gaa cgc gca att gca    1920
Glu Ile Val Glu Asn Met Ile Lys Ser Ser Leu Glu Arg Ala Ile Ala
625                 630                 635                 640 gcc tat acg cca aga gaa gag ctt cct gag gag tgg aag ctt gac ggt    1968
Ala Tyr Thr Pro Arg Glu Glu Leu Pro Glu Glu Trp Lys Leu Asp Gly
            645                 650                 655 cta gtt gat ctt atc aac aca act tat ctt gat gaa ggt gca ctt gag    2016
Leu Val Asp Leu Ile Asn Thr Thr Tyr Leu Asp Glu Gly Ala Leu Glu
        660                 665                 670 aag agc gat atc ttc ggc aaa gaa ccg gat gaa atg ctt gag ctc att    2064
Lys Ser Asp Ile Phe Gly Lys Glu Pro Asp Glu Met Leu Glu Leu Ile
    675                 680                 685 atg gat cgc atc atc aca aaa tat aat gag aag gaa gag caa ttc ggc    2112
Met Asp Arg Ile Ile Thr Lys Tyr Asn Glu Lys Glu Glu Gln Phe Gly
690                 695                 700 aaa gag caa atg cgc gaa ttc gaa aaa gtt atc gtt ctt cgt gcc gtt    2160
Lys Glu Gln Met Arg Glu Phe Glu Lys Val Ile Val Leu Arg Ala Val
705                 710                 715                 720 gat tct aaa tgg atg gat cat att gat gcg atg gat cag ctc cgc caa    2208
Asp Ser Lys Trp Met Asp His Ile Asp Ala Met Asp Gln Leu Arg Gln
            725                 730                 735 ggg att cac ctt cgt gct tac gcg cag acg aac ccg ctt cgt gag tat    2256
Gly Ile His Leu Arg Ala Tyr Ala Gln Thr Asn Pro Leu Arg Glu Tyr
        740                 745                 750 caa atg gaa ggt ttt gcg atg ttt gag cat atg att gaa tca att gag    2304
Gln Met Glu Gly Phe Ala Met Phe Glu His Met Ile Glu Ser Ile Glu
    755                 760                 765 gac gaa gtc gca aaa ttt gtg atg aaa gct gag att gaa aac aat ctg    2352
Asp Glu Val Ala Lys Phe Val Met Lys Ala Glu Ile Glu Asn Asn Leu
770                 775                 780 gag cgt gaa gag gtt gta caa ggt caa aca aca gct cat cag ccg caa    2400
Glu Arg Glu Glu Val Val Gln Gly Gln Thr Thr Ala His Gln Pro Gln
785                 790                 795                 800 gaa ggc gac gat aac aaa aaa gca aag aaa gca ccg gtt cgc aaa gtg    2448
Glu Gly Asp Asp Asn Lys Lys Ala Lys Lys Ala Pro Val Arg Lys Val
            805                 810                 815 gtt gat atc gga cga aat gcc cca tgc cac tgc gga agc ggg aaa aaa    2496
Val Asp Ile Gly Arg Asn Ala Pro Cys His Cys Gly Ser Gly Lys Lys
        820                 825                 830 tat aaa aat tgc tgc ggc cgt act gaa                                2523
Tyr Lys Asn Cys Cys Gly Arg Thr Glu
    835                 840

<210> SEQ ID NO 2
<211> LENGTH: 841
<212> TYPE: PRT
<213> ORGANISM: Bacillus subtilis

<400> SEQUENCE: 2

Met Leu Gly Ile Leu Asn Lys Met Phe Asp Pro Thr Lys Arg Thr Leu
1               5                   10                  15

Asn Arg Tyr Glu Lys Ile Ala Asn Asp Ile Asp Ala Ile Arg Gly Asp
```

-continued

```
                20                  25                  30
Tyr Glu Asn Leu Ser Asp Asp Ala Leu Lys His Lys Thr Ile Glu Phe
             35                  40                  45
Lys Glu Arg Leu Glu Lys Gly Ala Thr Thr Asp Asp Leu Leu Val Glu
 50                  55                  60
Ala Phe Ala Val Val Arg Glu Ala Ser Arg Arg Val Thr Gly Met Phe
 65                  70                  75                  80
Pro Phe Lys Val Gln Leu Met Gly Gly Val Ala Leu His Asp Gly Asn
                 85                  90                  95
Ile Ala Glu Met Lys Thr Gly Gly Lys Thr Leu Thr Ser Thr Leu
                100                 105                 110
Pro Val Tyr Leu Asn Ala Leu Thr Gly Lys Gly Val His Val Val Thr
            115                 120                 125
Val Asn Glu Tyr Leu Ala Ser Arg Asp Ala Glu Gln Met Gly Lys Ile
        130                 135                 140
Phe Glu Phe Leu Gly Leu Thr Val Gly Leu Asn Leu Asn Ser Met Ser
145                 150                 155                 160
Lys Asp Glu Lys Arg Glu Ala Tyr Ala Ala Asp Ile Thr Tyr Ser Thr
                165                 170                 175
Asn Asn Glu Leu Gly Phe Asp Tyr Leu Arg Asp Asn Met Val Leu Tyr
            180                 185                 190
Lys Glu Gln Met Val Gln Arg Pro Leu His Phe Ala Val Ile Asp Glu
        195                 200                 205
Val Asp Ser Ile Leu Ile Asp Glu Ala Arg Thr Pro Leu Ile Ile Ser
    210                 215                 220
Gly Gln Ala Ala Lys Ser Thr Lys Leu Tyr Val Gln Ala Asn Ala Phe
225                 230                 235                 240
Val Arg Thr Leu Lys Ala Glu Lys Asp Tyr Thr Tyr Asp Ile Lys Thr
                245                 250                 255
Lys Ala Val Gln Leu Thr Glu Glu Gly Met Thr Lys Ala Glu Lys Ala
            260                 265                 270
Phe Gly Ile Asp Asn Leu Phe Asp Val Lys His Val Ala Leu Asn His
        275                 280                 285
His Ile Asn Gln Ala Leu Lys Ala His Val Ala Met Gln Lys Asp Val
    290                 295                 300
Asp Tyr Val Val Glu Asp Gly Gln Val Val Ile Val Asp Ser Phe Thr
305                 310                 315                 320
Gly Arg Leu Met Lys Gly Arg Arg Tyr Ser Glu Gly Leu His Gln Ala
                325                 330                 335
Ile Glu Ala Lys Glu Gly Leu Glu Ile Gln Asn Glu Ser Met Thr Leu
            340                 345                 350
Ala Thr Ile Thr Phe Gln Asn Tyr Phe Arg Met Tyr Glu Lys Leu Ala
        355                 360                 365
Gly Met Thr Gly Thr Ala Lys Thr Glu Glu Glu Phe Arg Asn Ile
            370                 375                 380
Tyr Asn Met Gln Val Val Thr Ile Pro Thr Asn Arg Pro Val Val Arg
385                 390                 395                 400
Asp Asp Arg Pro Asp Leu Ile Tyr Arg Thr Met Glu Gly Lys Phe Lys
                405                 410                 415
Ala Val Ala Glu Asp Val Ala Gln Arg Tyr Met Thr Gly Gln Pro Val
            420                 425                 430
Leu Val Gly Thr Val Ala Val Glu Thr Ser Glu Leu Ile Ser Lys Leu
        435                 440                 445
```

-continued

Leu Lys Asn Lys Gly Ile Pro His Gln Val Leu Asn Ala Lys Asn His
450                     455                 460

Glu Arg Glu Ala Gln Ile Ile Glu Glu Ala Gly Gln Lys Gly Ala Val
465                 470                 475                 480

Thr Ile Ala Thr Asn Met Ala Gly Arg Gly Thr Asp Ile Lys Leu Gly
                485                 490                 495

Glu Gly Val Lys Glu Leu Gly Gly Leu Ala Val Val Gly Thr Glu Arg
                500                 505                 510

His Glu Ser Arg Arg Ile Asp Asn Gln Leu Arg Gly Arg Ser Gly Arg
            515                 520                 525

Gln Gly Asp Pro Gly Ile Thr Gln Phe Tyr Leu Ser Met Glu Asp Glu
530                 535                 540

Leu Met Arg Arg Phe Gly Ala Glu Arg Thr Met Ala Met Leu Asp Arg
545                 550                 555                 560

Phe Gly Met Asp Asp Ser Thr Pro Ile Gln Ser Lys Met Val Ser Arg
                565                 570                 575

Ala Val Glu Ser Ser Gln Lys Arg Val Glu Gly Asn Asn Phe Asp Ser
                580                 585                 590

Arg Lys Gln Leu Leu Gln Tyr Asp Asp Val Leu Arg Gln Gln Arg Glu
            595                 600                 605

Val Ile Tyr Lys Gln Arg Phe Glu Val Ile Asp Ser Glu Asn Leu Arg
610                 615                 620

Glu Ile Val Glu Asn Met Ile Lys Ser Ser Leu Glu Arg Ala Ile Ala
625                 630                 635                 640

Ala Tyr Thr Pro Arg Glu Glu Leu Pro Glu Glu Trp Lys Leu Asp Gly
                645                 650                 655

Leu Val Asp Leu Ile Asn Thr Thr Tyr Leu Asp Glu Gly Ala Leu Glu
                660                 665                 670

Lys Ser Asp Ile Phe Gly Lys Glu Pro Asp Glu Met Leu Glu Leu Ile
            675                 680                 685

Met Asp Arg Ile Ile Thr Lys Tyr Asn Glu Lys Glu Glu Gln Phe Gly
            690                 695                 700

Lys Glu Gln Met Arg Glu Phe Glu Lys Val Ile Val Leu Arg Ala Val
705                 710                 715                 720

Asp Ser Lys Trp Met Asp His Ile Asp Ala Met Asp Gln Leu Arg Gln
                725                 730                 735

Gly Ile His Leu Arg Ala Tyr Ala Gln Thr Asn Pro Leu Arg Glu Tyr
            740                 745                 750

Gln Met Glu Gly Phe Ala Met Phe Glu His Met Ile Glu Ser Ile Glu
            755                 760                 765

Asp Glu Val Ala Lys Phe Val Met Lys Ala Glu Ile Glu Asn Asn Leu
770                 775                 780

Glu Arg Glu Glu Val Val Gln Gly Gln Thr Thr Ala His Gln Pro Gln
785                 790                 795                 800

Glu Gly Asp Asp Asn Lys Lys Ala Lys Lys Ala Pro Val Arg Lys Val
                805                 810                 815

Val Asp Ile Gly Arg Asn Ala Pro Cys His Cys Gly Ser Gly Lys Lys
            820                 825                 830

Tyr Lys Asn Cys Cys Gly Arg Thr Glu
        835                 840

<210> SEQ ID NO 3
<211> LENGTH: 35
<212> TYPE: DNA
<213> ORGANISM: Artificial

```
<220> FEATURE:
<223> OTHER INFORMATION: Oligonucleotide as PCR primer designed from
      the nucleotide sequence of Bacillus subtilis gene, secA and
      added HindIII site sequence

<400> SEQUENCE: 3
gatcaagctt cccgggagaa gagcgatatc ttcgg                                  35

<210> SEQ ID NO 4
<211> LENGTH: 37
<212> TYPE: DNA
<213> ORGANISM: Artificial
<220> FEATURE:
<223> OTHER INFORMATION: Oligonucleotide as PCR primer designed from
      the nucleotide sequence of Bacillus subtilis gene, secA and
      added XbaI site sequence

<400> SEQUENCE: 4
gatcagatct agattaaatc tcagctttca tcacaaa                                37

<210> SEQ ID NO 5
<211> LENGTH: 35
<212> TYPE: DNA
<213> ORGANISM: Artificial
<220> FEATURE:
<223> OTHER INFORMATION: Oligonucleotide as PCR primer designed from
      the nucleotide sequence of Bacillus subtilis gene, secA and
      added HindIII site sequence

<400> SEQUENCE: 5
gatcaagctt cccgggagaa gagcgatatc ttcgg                                  35

<210> SEQ ID NO 6
<211> LENGTH: 37
<212> TYPE: DNA
<213> ORGANISM: Artificial
<220> FEATURE:
<223> OTHER INFORMATION: Oligonucleotide as PCR primer designed from
      the nucleotide sequence of Bacillus subtilis gene, secA and
      added XbaI site sequence

<400> SEQUENCE: 6
gatcagatct agattagata tcaaccactt tgcgaac                                37

<210> SEQ ID NO 7
<211> LENGTH: 25
<212> TYPE: DNA
<213> ORGANISM: Artificial
<220> FEATURE:
<223> OTHER INFORMATION: Oligonucleotide as PCR primer designed from
      the nucleotide sequence of Bacillus subtilis gene, amyE and
      added SpeI site sequence

<400> SEQUENCE: 7
ggccactagt cttcaaaaaa tcaaa                                             25

<210> SEQ ID NO 8
<211> LENGTH: 28
<212> TYPE: DNA
<213> ORGANISM: Artificial
<220> FEATURE:
<223> OTHER INFORMATION: Oligonucleotide as PCR primer designed from
      the nucleotide sequence of Bacillus subtilis gene, amyE and
      added KpnI site sequence

<400> SEQUENCE: 8
ggccggtacc ctcattcgat ttgttcgc                                          28
```

```
<210> SEQ ID NO 9
<211> LENGTH: 28
<212> TYPE: DNA
<213> ORGANISM: Artificial
<220> FEATURE:
<223> OTHER INFORMATION: Oligonucleotide as PCR primer designed from
      the nucleotide sequence of Bacillus subtilis gene, hIFN alpha
      and added KpnI site sequence

<400> SEQUENCE: 9
ggccggtacc ctcctggtgc tcagctgc                                           28

<210> SEQ ID NO 10
<211> LENGTH: 28
<212> TYPE: DNA
<213> ORGANISM: Artificial
<220> FEATURE:
<223> OTHER INFORMATION: Oligonucleotide as PCR primer designed from
      the nucleotide sequence of Bacillus subtilis gene, hIFN alpha
      and added BamHI site sequence

<400> SEQUENCE: 10
ggccggatcc ttttcattcc ttacttct                                           28

<210> SEQ ID NO 11
<211> LENGTH: 24
<212> TYPE: DNA
<213> ORGANISM: Artificial
<220> FEATURE:
<223> OTHER INFORMATION: Oligonucleotide as PCR primer designed from
      the nucleotide sequence of Bacillus subtilis gene, hIFN beta and
      added KpnI site sequence

<400> SEQUENCE: 11
ggccggtacc atgagctaca actt                                               24

<210> SEQ ID NO 12
<211> LENGTH: 28
<212> TYPE: DNA
<213> ORGANISM: Artificial
<220> FEATURE:
<223> OTHER INFORMATION: Oligonucleotide as PCR primer designed from
      the nucleotide sequence of Bacillus subtilis gene, hIFN beta and
      added BamHI site sequence

<400> SEQUENCE: 12
ggccggatcc agctcagttt cggaggta                                           28
```